United States Patent

Seed et al.

[11] Patent Number: 5,547,660
[45] Date of Patent: Aug. 20, 1996

[54] NAIL LACQUER COMPOSITION CONTAINING POLY-HYDROXYSTYRENE

[75] Inventors: John Seed, Ellicott City, Md.; Brian Seed, Boston, Mass.

[73] Assignee: Advanced Genetic Technologies Corporation, Gaithersburg, Md.

[21] Appl. No.: 229,089

[22] Filed: Apr. 18, 1994

Related U.S. Application Data

[63] Continuation-in-part of Ser. No. 981,094, Nov. 24, 1992, abandoned.

[51] Int. Cl.$^6$ ................................................. A61K 7/043
[52] U.S. Cl. ................................................. 424/61; 424/401
[58] Field of Search ................................ 424/61, 401

[56] References Cited

U.S. PATENT DOCUMENTS

| | | | |
|---|---|---|---|
| 3,150,048 | 9/1964 | Hollub et al. | 424/61 |
| 3,441,645 | 4/1969 | McKissick et al. | 424/61 |
| 3,483,289 | 12/1969 | Michaelson et al. | 424/61 |
| 3,749,769 | 7/1973 | Sugiyama et al. | 424/61 |
| 3,849,547 | 11/1974 | Kalopissis et al. | 424/61 |
| 3,864,294 | 2/1975 | Busch, Jr. | 106/271 |
| 4,600,030 | 7/1986 | Newman | 132/320 |
| 4,649,045 | 3/1987 | Gaske et al. | 424/61 |
| 4,880,487 | 11/1989 | Sheehan et al. | 156/327 |
| 5,087,772 | 2/1992 | Sheehan et al. | 568/804 |
| 5,264,206 | 11/1993 | Bohn et al. | 424/61 |
| 5,302,380 | 4/1994 | Castrogiovanni et al. | 424/63 |

FOREIGN PATENT DOCUMENTS

| | | |
|---|---|---|
| 524800-A1 | 1/1993 | European Pat. Off. . |
| 605951-A1 | 7/1994 | European Pat. Off. . |
| 04264003 | 9/1992 | Japan . |
| 04312503 | 11/1992 | Japan . |
| 04321610 | 11/1992 | Japan . |

*Primary Examiner*—John C. Bleutge
*Assistant Examiner*—Robert H. Harrison
*Attorney, Agent, or Firm*—Banner & Allegretti, Ltd.

[57] ABSTRACT

A nail polish composition with increased adhesiveness and durability is provided by the inclusion of compounds containing hydroxyl substituted aromatic groups, in particular protein-adherent polymers comprised of hydroxyl substituted aromatic groups.

1 Claim, No Drawings

NAIL LACQUER COMPOSITION CONTAINING POLY-HYDROXYSTYRENE

This application is a continuation-in-part of Ser. No. 981,094, which was filed Nov. 24, 1992, now abandoned.

TECHNICAL FIELD OF THE INVENTION

This invention relates to nail polish compositions with increased adhesiveness and durability.

BACKGROUND OF THE INVENTION

A variety of different polymer-containing formulations are known in the art for the preparation of glossy, adherent nail coatings. Typically, these are film-forming compositions which contain nitrocellulose, polymeric resins, solvents and pigments. The compositions may be supplemented with other materials such as sunscreens, fats, gelatin, vitamins and protein hydrolysates.

There are several limitations common to existing nail polishes. One of the most important limitations is the circumscribed resilience and adhesiveness of the polish. Thus, conventional polishes are susceptible to cracking and flaking; frequently the polish no longer serves a cosmetic role within two days of application and must be replaced. Increased durability can be achieved by using multiple layers of a polish or by purchasing specialized, multilayered polishes which are expensive, time consuming to apply and may require the use of specialized devices for drying and/or curing the polish.

The adhesive properties of many conventional nail polishes are believed to be a function of the affinity of nitrocellulose (the principle film-forming agent in conventional polishes) for protein. There is a need in the art for a polish with increased adhesive properties which can be applied in a single coat while retaining the characteristics of exceptional durability and high gloss.

SUMMARY OF THE INVENTION

It is an object of the invention to provide a nail polish with improved adhesion, which is durable and glossy.

This object is met by a nail lacquer composition which comprises a protein-adherent polymer comprising aromatic monomeric units, said monomeric units substituted on the aromatic moiety with at least one hydroxyl group.

DETAILED DESCRIPTION OF THE INVENTION

It is a finding of the present invention that compounds containing aromatic hydroxyl moieties are favorable components for nail lacquers, and particularly that protein-adherent polymers comprising hydroxyl-substituted aromatic moieties can be incorporated in nail polishes to yield compositions which when applied to nails have improved adhesion and durability as well as high gloss. Such protein-adherent polymers comprise a favorable proportion of aromatic monomeric units, substituted on the aromatic moiety with at least one hydroxyl group. The pK of the hydroxyl group is generally less than 11.

Aromatic monomeric units according to the present invention are chemical structures which have a resonance stabilized, conjugated ring system. The resonance stabilized, conjugated ring structure is preferably planar. The aromatic moiety is preferably a phenyl group. Suitable aromatic monomeric units include hydroxyphenyl-containing groups, especially para-hydroxyphenyl groups. The hydroxylated aromatic moiety is typically an integral part of the polymer and covalently linked to the polymer backbone, but may be linked to the polymer by ionic or strong noncovalent interactions such as hydrophobic stacking interactions.

Substitutions on the aromatic moiety or on the polymer backbone which do not substantially impair the protein binding properties of the polymer may be useful for modulating properties of the applied lacquer. Such properties include resilience, gloss, or ease of application. Similarly, properties of the un-applied lacquer can be modulated including solubility in desirable solvents, ease of composition or resistance to oxidation or degradation. The polymer comprising hydroxyl-substituted aromatic moieties may be a copolymer such as a random copolymer, a block copolymer, or a graft copolymer. A preferred monomer for inclusion in such polymers is 4-hydroxystyrene.

Although proteins contain hydroxyl-substituted aromatic moieties in the form of tyrosine residues, proteins in general do not bestow a favorable adhesiveness and durability on the film-forming compositions of the invention. A likely explanation is that ordinary proteins, i.e. those not specifically selected with the object of increased nail lacquer adhesion and durability, possess a limited proportion of tyrosine residues and such tyrosine residues are generally inaccessible to solvent and so cannot participate in the adhesive interaction. Peptides containing tyrosine may, however, be adhesive if designed or selected for the present purposes, as exemplified by peptide adhesives based on the naturally occurring adherent secretions of marine mollusks.

The material of the present invention is formulated as a solution or emulsion and includes as its primary active ingredient the hydroxyl-bearing aromatic moieties described above. It will have one or more diluents and also may include other polymers, plasticizers, preservatives, thickening agents, dyes, surface conditioning agents, emulsifiers, inorganic ions, and proteinaceous materials such as amino acids, proteins and peptides. Typically the formulation will be prepared in an organic solvent or solvent mixture in which the polymer is soluble. Suitable organic solvents include ethanol, ethoxyethanol, isopropanol, butyl acetate, ethyl acetate and acetone. Other solvents and solvent mixtures will be obvious to those skilled in the art. Polish compositions of the invention will typically contain between 0.5 and 40% by weight of the polymer comprising hydroxyl-substituted aromatic moieties of the invention. Preferably, the composition will contain at least 1%, and more preferably it will contain at least 10% by weight of the polymer. Compositions with high solids content can produce a glossy, smooth nail coating with a single application. The solids content and viscosity of the polish can be controlled by varying the size of the polymer and the solvent composition. The lower the molecular weight of the polymer, the higher the solids content which can be achieved for a polish of standardized viscosity.

Films formed by homopolymers of the invention tend to be brittle and susceptible to cracking. This difficulty can be obviated by the inclusion of plasticizing agents in the lacquer formulation. Suitable plasticizers include those known in the art, such as substituted phthalates and adipates, alcohol fatty acid esters and castor oil. Other materials which are suitable for plasticizing films of the invention include polyalkylene glycol esters, C8 and higher chain length alcohols and polybutadiene oxides of nominal molecular mass less than 2400 daltons. Plasticizing agents are typically added in amounts of 5–40% of the total solids content of the polish. Other film-forming resins may be incorporated in the nail polish formulation. Examples include nitrocellulose and toluene sulfonamide/formaldehyde resins. The invention is illustrated with the following examples which should not be construed as limiting.

EXAMPLES

EXAMPLE 1

Poly(4-hydroxystyrene) (MW 108,000) was dissolved at a concentration of 150 mg/ml in ethanol containing 0.01M $MgCl_2$ and coated onto fingernails. The resulting finish dried within 2 minutes and was clear, hard, glossy and could not be scraped or peeled off the nail. The nails could be trimmed, clipped or filed without cracking or chipping the finish. After 24 hours, some evidence of cracking was apparent at the base of the nail. Nevertheless, nails still could be trimmed, clipped or filed without peeling or chipping the finish at this time.

EXAMPLE 2

Poly(4-hydroxystyrene) was dissolved at a concentration of 150 mg/ml in ethanol containing 1% 2-ethyl-1,3-hexanediol and coated onto fingernails. The resulting finish dried within 2 minutes and was clear, hard, glossy and could not be scraped or peeled off the nail. The nails could be trimmed, clipped or filed without cracking or chipping the finish. After 48 hours, some evidence of cracking was apparent at the base of the nail. A conventional nail polish readily peeled at the base of the nail and chipped at the tip between 24 and 48 hours after application.

EXAMPLE 3

Poly(4-hydroxystyrene) was dissolved at a concentration of 100 mg/ml in acetone containing 10% Pluronic F68 and coated onto fingernails. The resulting finish dried within 1 minute and was clear, hard, glossy and could not be scraped or peeled off the nail. The nails could be trimmed, clipped or filed without cracking or chipping the finish. After 48 hours, some evidence of cracking was apparent at the base of the nail.

EXAMPLE 4

Poly(4-hydroxystyrene) was dissolved at a concentration of 200 mg/ml in n-butyl acetate/isopropanol (9:1). Polybutadiene oxide was added to the solution at a concentration of 80 mg/ml. The resulting viscous solution was applied to nails. The resulting finish dried within 15 minutes and was clear, hard, smooth, highly glossy and could not be scraped or peeled off the nail for at least 5 days. The nails could be trimmed, clipped or filed without cracking or chipping the finish. After 72 hours, some evidence of microscopic cracking was apparent at the base of the nail.

EXAMPLE 5

Poly(4-hydroxystyrene) was dissolved at a concentration of 200 mg/ml in n-butyl acetate/isopropanol (9:1). Di-n-butyl phthalate was added to the solution at a concentration of 40 mg/ml. D & C Red 27 aluminum lake was added at a concentration of 1 mg/ml and mixed until homogeneous. The resulting viscous solution was applied to nails. The resulting finish was smooth, hard, highly glossy and could not be scraped or peeled off the nail for at least 5 days.

EXAMPLE 6

Poly(4-hydroxystyrene) was dissolved at a concentration of 200 mg/ml in n-butyl acetate/isopropanol (1:1). Di-n-butyl phthalate was added to the solution at a concentration of 40 mg/ml. The resulting viscous solution was applied to nails in a single coat. The resulting finish dried within 15 minutes and was clear, hard, smooth, highly glossy and could not be scraped or peeled off the nail for at least 5 days.

EXAMPLE 7

Poly(4-hydroxystyrene) was dissolved at a concentration of 250 mg/ml in toluene/n-butyl acetate/ethanol/water (100:500:190:10, v:v). Di-n-butyl phthalate and polyethyleneglycol(600)-dibenzoate were added to the solution at a concentration of 40 mg/ml each. D & C Red #7 calcium lake was added at 10 mg/ml. The resulting viscous solution was applied to nails in a single coat. The resulting finish dried to the touch within 10 minutes and was clear, hard, smooth and highly glossy.

We claim:

1. A method of cosmetically coating nails, comprising:
   applying to nails a composition comprising:
   (a) a protein-adherent polymer consisting of poly(4-hydroxystyrene) wherein said protein-adherent polymer is present at amounts of 0.5–40% by weight in said composition so that said protein-adherent polymer forms a film upon application to a nail;
   (b) a plasticizing agent which is present in amounts of 5–40% based on the total solids content of the composition; and
   (c) a cosmetically acceptable diluent.

* * * * *